United States Patent
Redmond et al.

(10) Patent No.: US 11,564,767 B2
(45) Date of Patent: Jan. 31, 2023

(54) CLINICAL DIAGNOSIS AND TREATMENT PLANNING SYSTEM AND METHODS OF USE

(71) Applicant: Warsaw Orthopedic, Inc., Warsaw, IN (US)

(72) Inventors: Jerald Redmond, Germantown, TN (US); Thomas A. Carls, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 393 days.

(21) Appl. No.: 16/855,691

(22) Filed: Apr. 22, 2020

(65) Prior Publication Data

US 2021/0330416 A1  Oct. 28, 2021

(51) Int. Cl.
*A61B 90/00* (2016.01)
*A61B 5/00* (2006.01)
(Continued)

(52) U.S. Cl.
CPC ............ *A61B 90/36* (2016.02); *A61B 5/0064* (2013.01); *A61B 5/0077* (2013.01);
(Continued)

(58) Field of Classification Search
CPC ..... A61B 90/36; A61B 5/0064; A61B 5/0077; A61B 5/1077; A61B 5/1079; A61B 5/4566; A61B 5/745; A61B 34/10; A61B 2034/107; A61B 2090/365; A61B 2090/376; A61B 2090/502; A61B 90/361;
(Continued)

(56) References Cited

U.S. PATENT DOCUMENTS

| 9,220,536 | B2 * | 12/2015 | Skaggs ............. A61B 17/7022 |
| 9,248,000 | B2 | 2/2016 | Sarvestani et al. |
| 9,498,132 | B2 | 11/2016 | Maier-Hein et al. |
| 9,892,564 | B1 | 2/2018 | Cvetko |
| 10,010,379 | B1 | 7/2018 | Gibby |

(Continued)

FOREIGN PATENT DOCUMENTS

| CN | 108784832 | 11/2018 |
| CN | 110266992 | * 9/2019 ........... G06T 19/006 |

(Continued)

OTHER PUBLICATIONS

International Search Report and Written Opinion dated Aug. 6, 2021 issued by the International Searching Authority in corresponding International Application No. PCT/US2021/026440 filed Apr. 8, 2021.

*Primary Examiner* — Jerome Grant, II
(74) *Attorney, Agent, or Firm* — Sorell, Lenna & Schmidt, LLP

(57) ABSTRACT

A spinal disorder diagnosis and treatment planning system is provided. The diagnosis and treatment planning system includes a mixed reality holographic display including at least one processor, at least one camera, at least one sensor, and being configured to acquire data points corresponding to a surface of a body adjacent to vertebral tissue. A computer database is configured to transmit imaging of the body including the vertebral tissue to the mixed reality holographic display. The mixed reality holographic display is configured to display a first holographic image of the vertebral tissue superimposed with a body image including the surface. Methods are also disclosed.

20 Claims, 13 Drawing Sheets

(51) Int. Cl.
*A61B 34/10* (2016.01)
*A61B 5/107* (2006.01)
*A61B 90/50* (2016.01)

(52) U.S. Cl.
CPC .......... *A61B 5/1077* (2013.01); *A61B 5/1079* (2013.01); *A61B 5/4566* (2013.01); *A61B 5/745* (2013.01); *A61B 34/10* (2016.02); *A61B 2034/107* (2016.02); *A61B 2090/365* (2016.02); *A61B 2090/376* (2016.02); *A61B 2090/502* (2016.02)

(58) Field of Classification Search
CPC ...... A61B 2034/105; A61B 2034/2048; A61B 2090/371; A61B 2090/372
USPC ........................................................ 600/476
See application file for complete search history.

(56) References Cited

U.S. PATENT DOCUMENTS

| | | | |
|---|---|---|---|
| 10,013,808 | B2 | 7/2018 | Jones |
| 10,716,469 | B2 * | 7/2020 | Krueger ................. A61B 3/112 |
| 10,788,791 | B2 * | 9/2020 | Gelman ............... G03H 1/0005 |
| 11,273,003 | B1 * | 3/2022 | Haider ............... G02B 27/0093 |
| 2016/0278868 | A1 | 9/2016 | Berend et al. |
| 2019/0056693 | A1 | 2/2019 | Gelman et al. |
| 2019/0365498 | A1 | 12/2019 | Gibby et al. |
| 2020/0074748 | A1 * | 3/2020 | de Almeida Barreto ................... G06K 9/6276 |
| 2020/0268449 | A1 * | 8/2020 | Solitro .................. A61B 6/032 |

FOREIGN PATENT DOCUMENTS

| | | |
|---|---|---|
| JP | 2015-504320 | 2/2015 |
| WO | 2019-245861 | 12/2019 |

* cited by examiner

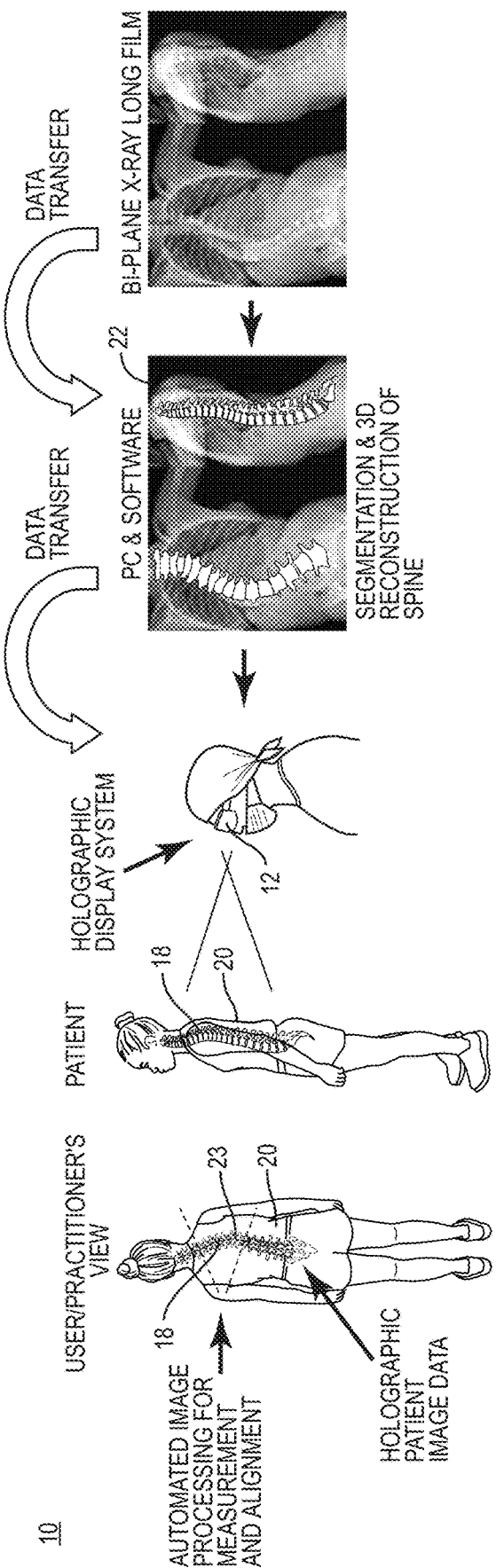
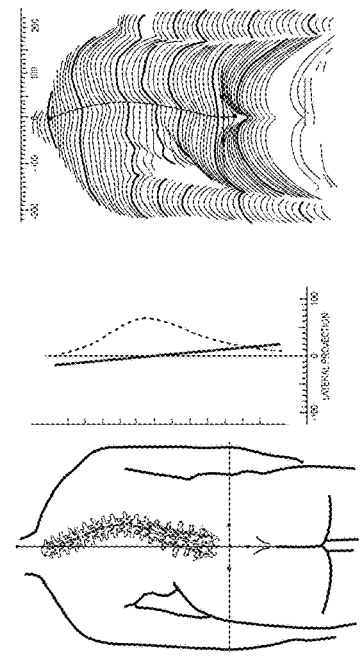
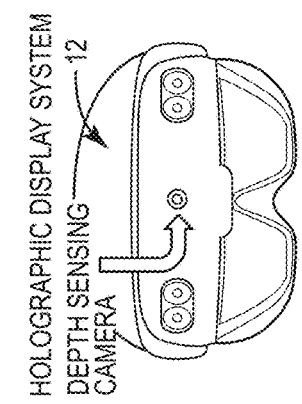
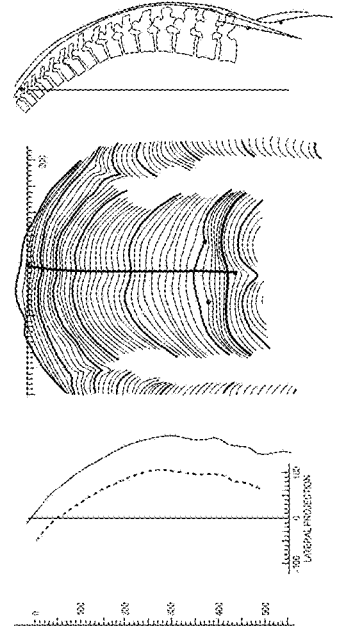
FIG. 10

CLINICAL DIAGNOSIS AND TREATMENT PLANNING SYSTEM AND METHODS OF USE

TECHNICAL FIELD

The present disclosure generally relates to medical systems for the diagnosis and treatment of musculoskeletal disorders, and more particularly to a system and method for spine disorder diagnosis and treatment planning.

BACKGROUND

Spinal disorders such as degenerative disc disease, disc herniation, osteoporosis, spondylolisthesis, stenosis, scoliosis and other curvature abnormalities, kyphosis, tumor and fracture may result from factors including trauma, disease and degenerative conditions caused by injury and aging. Spinal disorders typically result in symptoms including pain, nerve damage, and partial or complete loss of mobility.

Clinical evaluation and diagnosis of spinal disorders can be based on physical examination and medical imaging of a patient. Physical examination may include evaluation of physical limitations in range of motion, evidence of instability, observable deformities and patient pain responses. Such physical examination and medical imaging is employed to formulate clinical diagnosis and treatment planning for the patient. Treatment planning may include non-surgical treatments and/or surgical treatments of spinal disorders. Non-surgical treatment can include medication, rehabilitation and exercise, which can be effective, however, may fail to relieve the symptoms associated with these disorders. Surgical treatment of these spinal disorders includes correction, fusion, fixation, discectomy, laminectomy and implantable prosthetics. As part of these surgical treatments, interbody devices can be employed with spinal constructs, which include implants such as bone fasteners and vertebral rods to provide stability to a treated region. This disclosure describes an improvement over these prior technologies.

SUMMARY

In one embodiment, a spinal disorder diagnosis and treatment planning system is provided. The diagnosis and treatment planning system includes a mixed reality holographic display including at least one processor, at least one camera and at least one sensor. The mixed reality holographic display is configured to acquire data points corresponding to a surface of a body adjacent to vertebral tissue. A computer database is configured to transmit imaging of the body including the vertebral tissue to the mixed reality holographic display. The mixed reality holographic display is configured to display a first holographic image of the vertebral tissue superimposed with a body image including the surface. In some embodiments, methods are disclosed.

In one embodiment, the spinal disorder diagnosis and treatment planning system comprises a tangible storage device including computer-readable instructions. A mixed reality holographic headset includes a central processor and a holographic processor, and one or more cameras and sensors. One or more processors execute the instructions in operation of the system for: imaging a body including vertebral tissue in a non-surgical environment; scanning in real-time a surface of the body adjacent to the vertebral tissue with the mixed reality holographic headset; registering a first holographic image of the vertebral tissue with a body image of the scanned surface in a common coordinate system; and displaying in real-time the first holographic image and the body image in the common coordinate system with the mixed reality holographic headset.

In one embodiment, the spinal disorder diagnosis and treatment planning system comprises a tangible storage device comprising computer-readable instructions. A mixed reality holographic headset includes a central processor and a holographic processor, and one or more cameras and sensors. One or more processors, execute the instructions in operation of the system for: imaging a body including vertebral tissue in a non-surgical environment; scanning in real-time a surface of the body adjacent to the vertebral tissue with a mixed reality holographic headset; determining a surgical treatment configuration for the vertebral tissue; registering a first holographic image of the vertebral tissue and/or a second holographic image of the surgical treatment configuration with a body image of the scanned surface in a common coordinate system; and displaying in real-time the first holographic image and/or the second holographic image with the body image in the common coordinate system with the mixed reality holographic headset.

BRIEF DESCRIPTION OF THE DRAWINGS

The present disclosure will become more readily apparent from the specific description accompanied by the following drawings, in which:

FIG. 10 is a schematic diagram illustrating components of one embodiment of a diagnosis and treatment planning system including a representation of imaging and steps of one or more embodiments of a method in accordance with the principles of the present disclosure;

DETAILED DESCRIPTION

Figure 1:
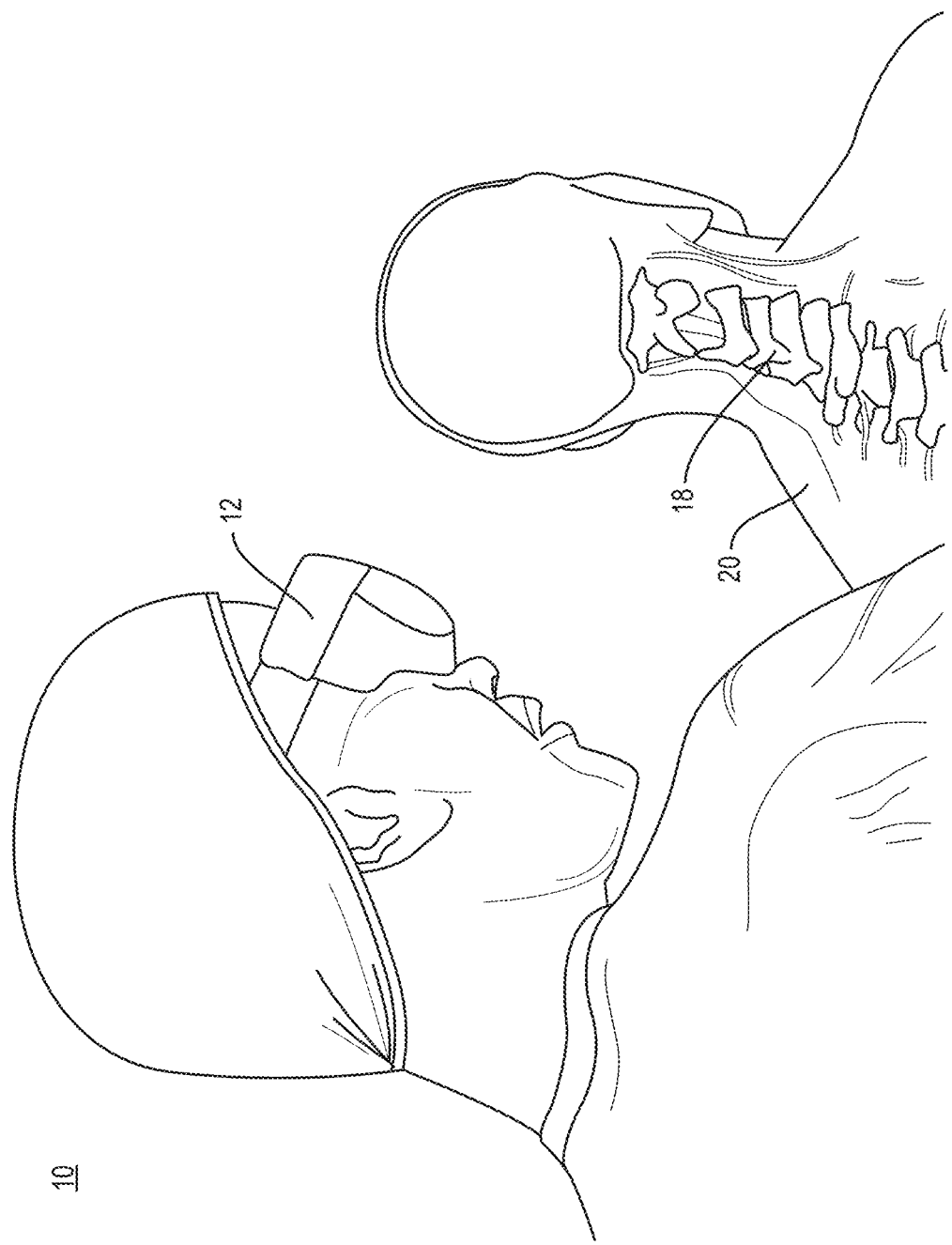
FIG. 1 is a perspective view of components of one embodiment of a diagnosis and treatment planning system in accordance with the principles of the present disclosure.

The exemplary embodiments of a spinal disorder diagnosis and treatment planning system are discussed in terms of medical devices for the treatment of musculoskeletal disorders and more particularly, in terms of a system and method for spine disorder diagnosis and treatment planning. In some embodiments, the present diagnosing and treatment planning system includes a mixed reality holographic display or an augmented reality holographic display, and is employed with a method for spinal disorder diagnosis and treatment planning, including superimposing a holographic image of a patient's vertebral tissue with a body image including the surface of the patient and correlating the images for real-time visualization of spine orientation and alignment.

In some embodiments, the present surgical system comprises a display including a holographic display device. In some embodiments, the systems and methods of the present disclosure comprise a mixed reality display or an augmented reality display employed with diagnosis and treatment planning, as described herein, for example, for a cervical, thoracic, lumbar and/or sacral region of a spine.

In some embodiments, the present diagnosis and treatment planning system and method includes imaging of a patient's vertebrae, for example, through two-dimensional (2D) imaging generated from radiography including, for example, an X-ray or a bi-plane X-ray long film. In some embodiments, the imaging is generated during patient movement, including, for example, flexation and/or extension. In some embodiments, a computer converts the imaging to digital data and transfers the digital data to a mixed reality headset, for example, a holographic headset. In some embodiments, the computer utilizes software to determine a surgical treatment configuration for the vertebral tissue through segmentation and/or three dimensional (3D) reconstruction of the vertebrae. In some embodiments, an image of the surgical treatment configuration is transmitted to the headset for display from the headset. In some embodiments, the image of the vertebrae with the body image and/or the surgical treatment configuration is holographically overlaid onto the actual patient, including, for example, a surface of the body of the patient. In some embodiments, the holographic overlays are implemented to view vertebral positioning, including for example, orientation and alignment on the patient. In some embodiments, the headset includes automated image processing for measurement and alignment of the vertebrae of the patient.

In some embodiments, the headset includes cameras, for example, one or more depth sensing cameras. In some embodiments, the one or more depth sensing cameras are configured to spatially map surfaces of the patient in an environment for localizing and displaying content. In some embodiments, recognition markers are positioned on objects, for example, a back surface of the patient that can be recognized by the cameras on the headset for displaying the content. In some embodiments, the content displayed is a map of the back of the patient. In some embodiments, the one or more depth sensing cameras provide a real-time update of a 3D vertebral model during a physical exam of the patient.

In some embodiments, the present diagnosis and treatment planning system includes a holographic display system that is implemented during an initial evaluation, including, for example, a physical examination for a surgical procedure such that the image of the vertebrae with the body image and/or the surgical treatment configuration is holographically overlaid onto the actual patient to dynamically visualize patient anatomy for optimizing diagnosis and treatment planning. In some embodiments, the images are integrated with the patient through a holographic overlay. In some embodiments, the holographic overlay includes images of the vertebrae with the body image and/or the surgical treatment configuration that is patient specific. In some embodiments, the image of the vertebrae with the body image and/or the surgical treatment configuration utilizes patient specific anatomy data generated from images, for example, radiography, including, for example, an X-ray or a bi-plane X-ray long film. In some embodiments, the holographic overlay is superimposed on a surface of the patient in the clinic prior to a surgical procedure for clinical diagnosis and treatment planning. In some embodiments, a surgical plan can be generated from images of the vertebrae with the body image and/or the surgical treatment configuration that is uploaded into a navigation and/or robotic system, including for example, Mazor X™ and/or Stealthstation™ sold by Medtronic Navigation, Inc. having a place of business in Louisville, Colo. when a surgical procedure is required.

In some embodiments, the present diagnosis and treatment planning system includes recognition markers positioned relative to the patient to map the surface of the patient. In some embodiments, a scanner is implemented to map the surface of the patient. In some embodiments, the holographic overlay is implemented in conjunction with depth sensing cameras and/or sensors for real-time visualization of vertebral orientation and alignment.

In some embodiments, the present diagnosis and treatment planning system and methods include spatially located 3D holograms, for example, holographic overlays for displaying image guidance information. In some embodiments, the present diagnosis and treatment planning system and methods include cameras, for example, depth sensing cameras. In some embodiments, the depth sensing cameras include infrared, laser, and/or red/green/blue (RGB) cameras. In some embodiments, depth sensing cameras along with simultaneous localization and mapping are employed to digitize the patient, spinal anatomy, and/or the clinic room for spatially locating holograms and then displaying the digital information holographically onto the patient and correlation of the image data with current patient anatomy for real-time visualization of spinal alignment. In some embodiments, the present diagnosis and treatment planning system and methods include software algorithms, for example, object recognition software algorithms that are implemented for spatially locating the holograms and for displaying digital information relative to patient anatomy. In some embodiments, machine learning algorithms are employed that identify patient anatomical structures in patient images for image segmentation and 3D model generation as well as to identify patient external anatomy for spatial placement of holographic images. In some embodiments, machine learning algorithms generate automated measurements of spinal alignment parameters in patient images, for example, including a cobb angle, pelvic tilt, pelvic incidence, sacral slope, lumbar lordosis, thoracic kyphosis, cervical lordosis, and/or sagittal vertical axis. In some embodiments, software algorithms are implemented in 3D image processing software employed for the surgical treatment configuration including for example, software algorithms for importing, thresholding, masking, segmentation, cropping, clipping, panning, zooming, rotating, measuring and/or registering.

In some embodiments, the present diagnosis and treatment planning system and methods include depth sensing cameras, for example, infrared, laser, and/or RGB cameras; spatial transducers, for example, electromagnetic, low energy Bluetooth®, and/or inertial measurement units; optical markers, for example, reflective spheres, QR codes/patterns, and/or fiducials; and/or object recognition software algorithms to track a spatial position of a patient, for example, a patient's vertebral bodies and update a digital representation in real time. In some embodiments, the present diagnosis and treatment planning system and methods include 3D imaging software algorithms implemented to render and display changes in an anatomical position in real-time. In some embodiments, the present diagnosis and treatment planning system and methods include holographic display technology, for example, optical waveguides to display holograms, image guidance, and/or other digital information in real-time.

In some embodiments, the present diagnosis and treatment planning system and methods include labeling, for example, annotating of 3D data and/or medical imaging of the patient's anatomy in real-time during a physical examination and/or in real-time, for example, to identify areas of interest and/or locations where a patient is experiencing pain. In some embodiments, during a physical examination and/or imaging while the patient is moving, for example, flexing and/or extending, a medical practitioner has the ability to label an area of interest and/or locations where a patient is experiencing pain. In some embodiments, the label assists the medical practitioner during a surgical procedure.

In some embodiments, the present diagnosis and treatment planning system and methods include a software program for processing of 2D images for example, radiography, including, for example, bi-plane X-ray long film images to reconstruct these images into 3D anatomy such that the practitioner has freedom to view the patient images from any angle/orientation and see anatomy data accurately positioned on the patient.

In some embodiments, the present diagnosis and treatment planning system and methods include real-time mapping of the patient's back curvature to update imaging of the patient's vertebrae as the patient is examined with flexation, extension and/or lateral bending maneuvers. In some embodiments, during imaging, patient anatomy is flexed at an appropriate location and is tracked with the patient's position as the practitioner examines the patient.

In some embodiments, the present diagnosis and treatment planning system is employed with methods for spinal disorder diagnosis and treatment planning. In some embodiments, the present diagnosis and treatment planning system is employed with methods including the step of imaging a body including vertebral tissue. In some embodiments, imaging is generated through 2D imaging generated from radiography, including, for example, an X-ray or a bi-plane X-ray long film. In some embodiments, the present diagnosis and treatment planning system is employed with methods including the step of acquiring data points corresponding to a surface of the body adjacent to the vertebral tissue with a mixed reality holographic display. In some embodiments, the present diagnosis and treatment planning system is employed with methods including the step of transmitting the imaging to a computer database. In some embodiments, a computer utilizes software to determine a surgical treatment configuration for the vertebral tissue through segmentation and/or 3D reconstruction of the vertebrae. In some embodiments, the present diagnosis and treatment planning system is employed with methods including the step of superimposing a holographic image of the vertebral tissue with a body image including the surface. In some embodiments, the present diagnosis and treatment planning system is employed with methods including the step of displaying the holographic image and the body image with the mixed reality holographic display. In some embodiments, the mixed reality holographic display system includes a processor, cameras, and sensors.

In some embodiments, the system of the present disclosure may be employed for diagnosing and treatment planning for spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a diagnosing and treatment planning with a patient in a prone or supine position, and/or employ various approaches to the spine, including anterior, posterior, posterior mid-line, direct lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a diagnosis and treatment planning system including mixed and/or augmented reality technology, holographic overlays, related components and methods of employing the diagnosis and treatment planning system in accordance with the principles of the present disclosure. Alternate embodiments are also disclosed. Reference is made in detail to the exemplary embodiments of the present disclosure, which are illustrated in the accompanying figures. Turning to FIGS. 1-10, there are illustrated components of a diagnosis and treatment planning system 10.

The components of diagnosis and treatment planning system 10 can be fabricated from biologically acceptable materials suitable for medical applications, including metals, synthetic polymers, ceramics and bone material and/or their composites. For example, the components of diagnosis and treatment planning system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

The components of diagnosis and treatment planning system 10, individually or collectively, may also be fabricated from a heterogeneous material such as a combination of two or more of the above-described materials. The components of diagnosis and treatment planning system 10 may be monolithically formed, integrally connected or include fastening elements and/or instruments, as described herein.

Diagnosis and treatment planning system 10 can be employed, for example, before a minimally invasive procedure, including percutaneous techniques, mini-open and open surgical techniques to manipulate tissue, deliver and introduce instrumentation and/or components of spinal constructs at a surgical site within a body of a patient, for example, a section of a spine.

Diagnosis and treatment planning system 10 is implemented during an initial evaluation, including, for example, during a physical examination for a surgical procedure such that imaging of patient vertebrae with a body image and/or a surgical treatment configuration can be holographically overlaid onto the actual patient to dynamically visualize patient anatomy for optimizing diagnosis and treatment planning. Diagnosis and treatment planning system 10 utilizes a mixed reality and/or augmented reality display, for example, to holographically overlay imaging of patient vertebrae with the body image and/or the surgical treatment configuration specific to a patient onto a surface of the patient to assist in diagnosing and treatment planning for the patient.

Figure 2:
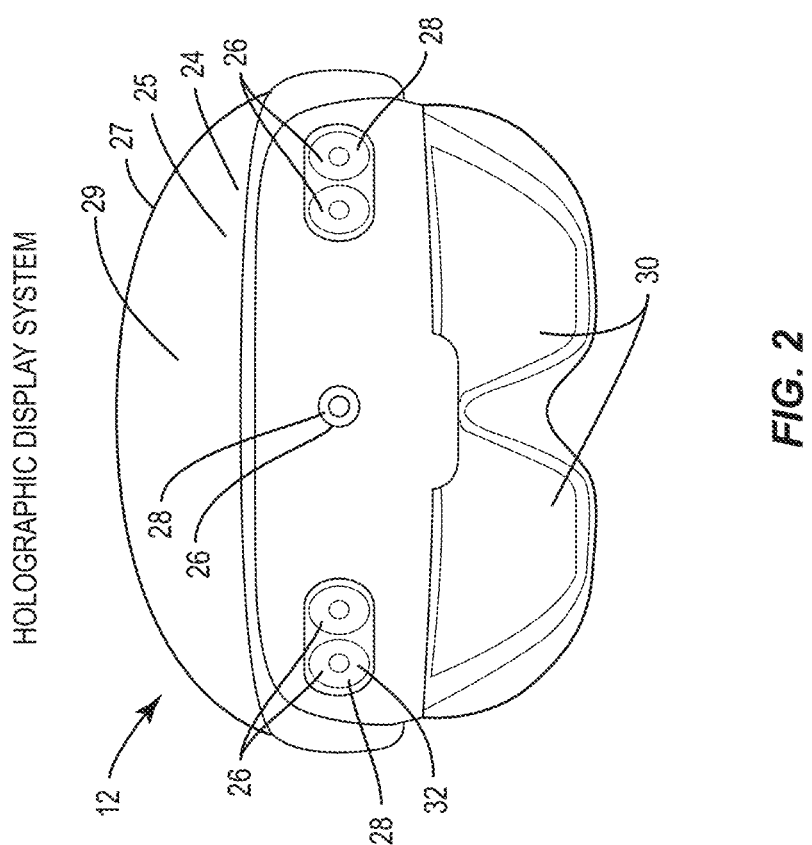
FIG. 2 is a plan view of components of one embodiment of a diagnosis and treatment planning system in accordance with the principles of the present disclosure.

Diagnosis and treatment planning system 10 includes a mixed reality holographic display, for example, an optical see-through headset 12, as shown in FIG. 2. Headset 12 is configured to acquire data points corresponding to a surface of a body of a patient adjacent to vertebral tissue. The data points include, for example, 3D mapping of the surface of the body. Headset 12 is configured to communicate with a database 14 loaded on a computer 42 that transmits imaging 16 of the body including the vertebral tissue to headset 12. Headset 12 is configured to display a holographic image 18 of the vertebral tissue superimposed with a body image 20 including the surface of the body in real-time. Headset 12 is configured to dynamically display in real-time orientation and alignment of the vertebral tissue in a non-surgical environment, for example, a clinic, medical practitioner office, examination room, hospital and/or medical evaluation and diagnosis facility prior to surgery as described herein.

Headset 12 is configured to display a surgical treatment configuration holographic image 23 superimposed with body image 20. Data points corresponding to the surface of the body of the patient adjacent to vertebral tissue are transmitted from headset 12 to database 14 such that database 14 can determine a surgical treatment configuration 22 for the vertebral tissue. The surgical treatment configuration data is then transferred to headset 12 for display as surgical treatment configuration image 23. The surgical treatment configuration 22 includes segmentation of the vertebral tissue and/or a surgical reconstruction of the vertebral tissue, as described herein and show in FIG. 4.

Headset 12 includes a processor 24, for example, a central processing unit (CPU). Processor 24 is configured to execute one or more instructions, for example, software instructions in operation of headset 12, as described herein. Processor 24 functions as the primary coordinating component of headset 12 and is configured to access programs, data, and/or other functions from random access memory (RAM) when called by an operating system (OS) of headset 12. Processor 24 interprets instructions that are related to ordered tasks before sending it back to the RAM for execution via a bus of headset 12 in the correct order of execution.

Headset 12 includes a rendering processor, for example, a graphics processor 25. Graphics processor 25 includes a graphics processing unit (GPU). Graphics processor 25 is configured to render images, animations and/or video for display on headset 12. In some embodiments, processor 24 instructs graphics processor 25 to render the images, animations and/or video. Images rendered include, for example, image 18 of the vertebral tissue, body image 20 and/or surgical treatment configuration image 23. Graphics processor 25 is configured to communicate with a camera 26 of headset 12 which captures a digital video image of the real world and transfers the digital video image to graphics processor 25 in real-time. Graphics processor 25 combines the video image feed with computer-generated images (e.g., virtual content), for example, image 18 of the vertebral tissue, body image 20 and/or surgical treatment configuration image 23 and displays the images on headset 12. In some embodiments, headset 12 alternatively or in addition to graphics processor 25 includes a holographic processor 27. Holographic processor 27, for example a holographic processing unit (HPU) is configured to conduct the processing that integrates digital video image data of the real world, data for augmented reality and/or user input (see, for example, the holographic processing unit sold by Microsoft Corporation, having a place of business in Redmond, Wash., USA).

Figure 8:
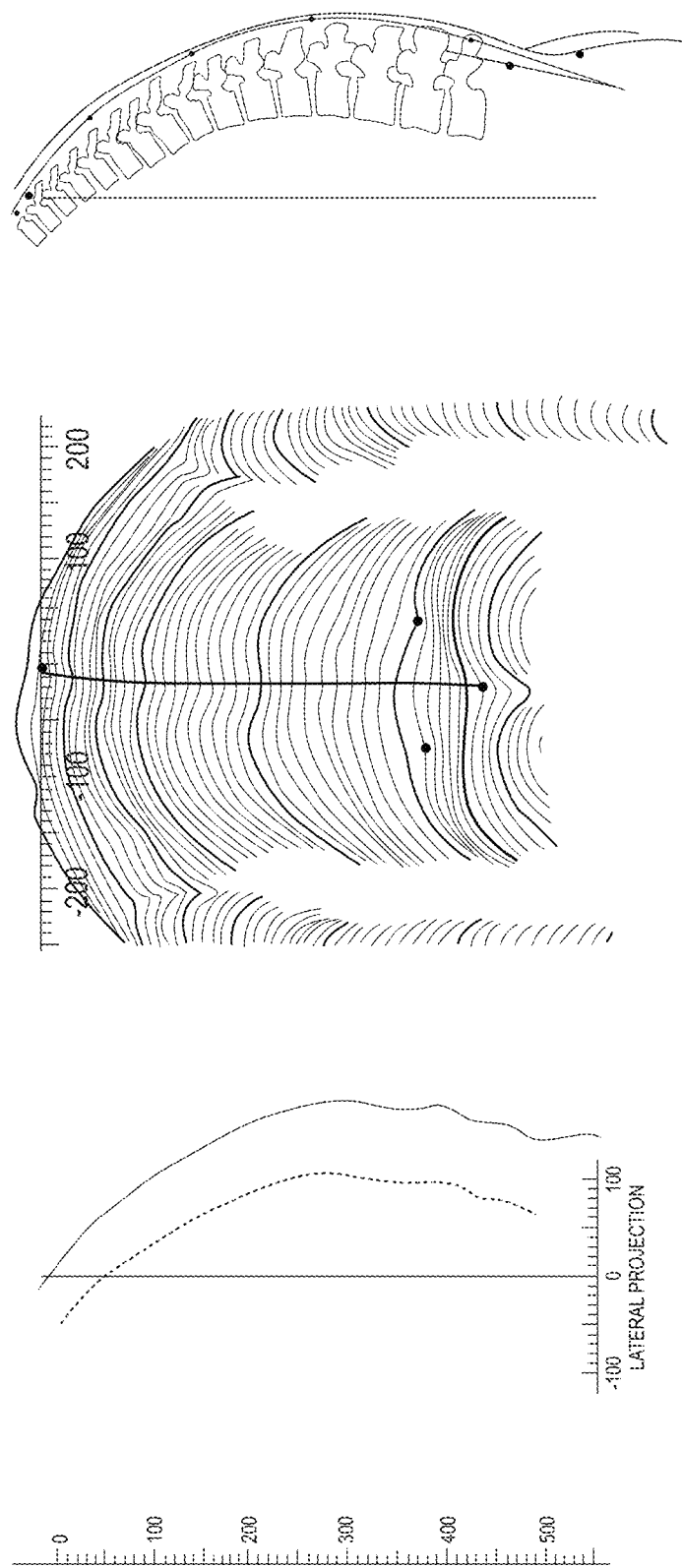
FIG. 8 is a schematic diagram illustrating components of one embodiment of a diagnosis and treatment planning system including a representation of imaging in accordance with the principles of the present disclosure.
Figure 9:
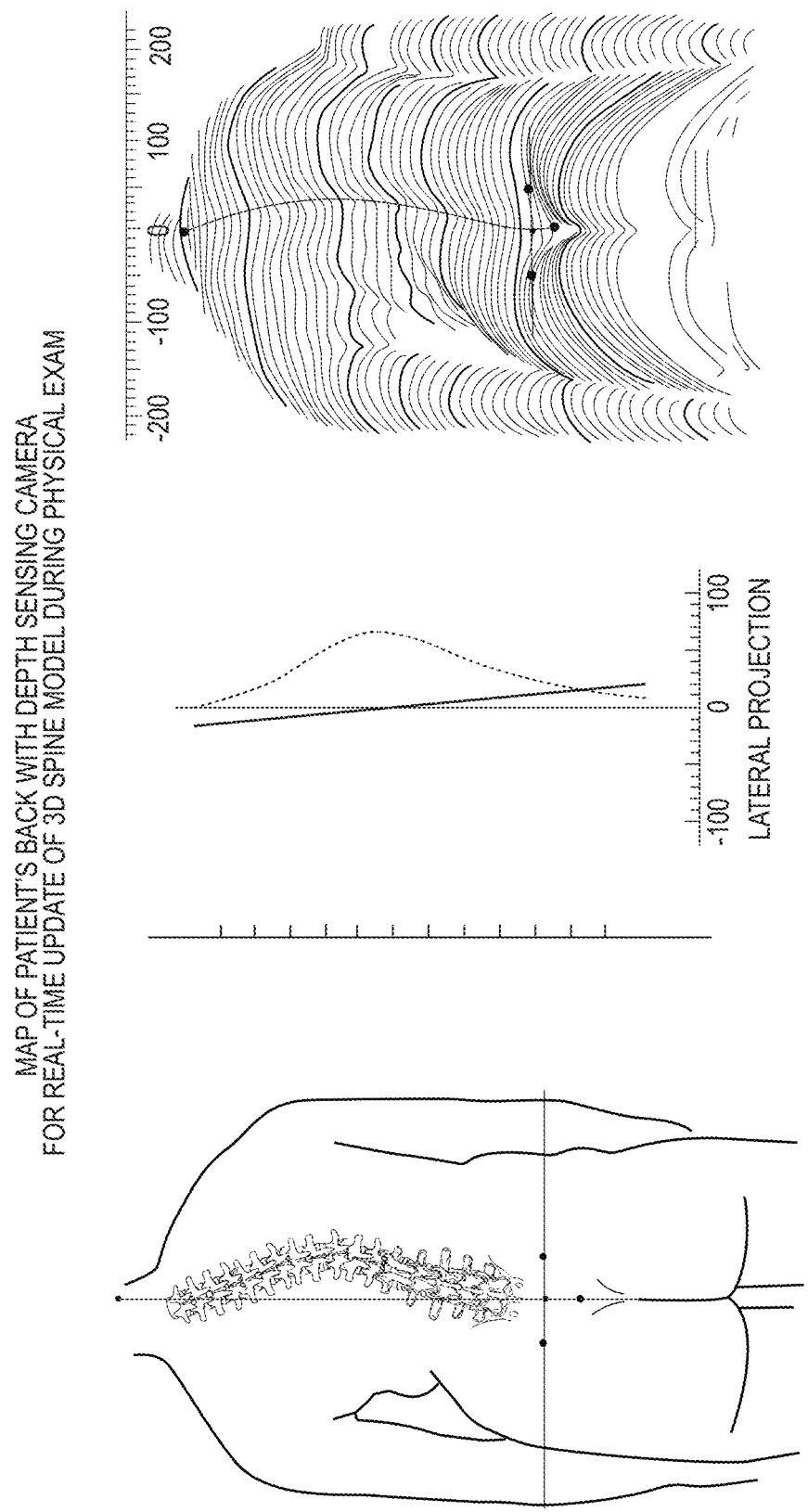
FIG. 9 is a schematic diagram illustrating components of one embodiment of a diagnosis and treatment planning system including a representation of imaging in accordance with the principles of the present disclosure.

Headset 12 includes camera 26, for example, a depth sensing camera. Camera 26 is disposed on a front side 29 of headset 12, as shown in FIG. 2. Camera 26 is configured to capture real-time digital video images of the patient, for example, the vertebral tissue and/or a map of a portion of the patient, including, for example, the patient's back for a real-time update of a 3D vertebral model during an examination, as shown in FIGS. 8 and 9 and/or real-time images of an external environment of the real world, for example, the clinic or examination room during an examination. The real-time images captured by camera 26 are outputted to headset 12 and displayed on a lens 30 of headset 12. The real-time images captured by camera 26, image 18 of the vertebral tissue, body image 20 and/or surgical treatment configuration image 23 rendered from graphics processor 25 are displayed concurrently. In some embodiments, camera 26 includes an environment camera. In some embodiments, the depth sensing camera can work in tandem with the environment camera. In some embodiments, the depth sensing camera includes infrared, laser, and/or RGB cameras. In some embodiments, camera 26 includes a stereoscopic camera, for example, a pair of cameras.

Headset 12 includes a sensor 28. Sensor 28 is disposed on front side 29 of headset 12 and is a component of camera 26, as shown in FIG. 2. Sensor 28 includes a 3D scanner 32 configured to determine and capture the 3D mapping of the surface of the body so that, for example, a real-time update of a 3D vertebral model of the patient can be displayed, as shown in FIGS. 8 and 9. 3D scanner 32 is configured to determine and capture the 3D mapping of the surface of the body so that image 18 of the vertebral tissue, body image 20, surgical treatment configuration image 23 and/or other images can be holographically overlaid onto the patient through headset 12. In some embodiments, camera 26 along with simultaneous localization and mapping implemented by 3D scanner 32 digitizes the patient, spinal anatomy, and/or the clinic or examination room for spatially locating holograms and then displays the digital information via lens 30 of headset 12. Digital video (e.g., stereoscopic video) combined with 3D mapping of the surface of the body determined by 3D scanner 32 and image 18 of the vertebral tissue, body image 20 and/or surgical treatment configuration image 23 is combined by graphics processor 25 for display.

In some embodiments, 3D scanner 32 implements simultaneous localization and mapping (SLAM) technology to determine 3D mapping of the surface of the body. SLAM technology simultaneously localizes (finds the location of an object/sensor with reference to its surroundings) and maps the layout and framework of the environment for headset 12. This can be done using a range of algorithms that simultaneously localize and map the objects.

In some embodiments, 3D mapping of the surface of the body can be determined through the use of 3D scanner 32, camera 26 and recognition markers (not shown) positioned relative to the patient and/or on a surface of the patient to map the surface of the patient. In some embodiments, the recognition markers may be attached to the patient to provide anatomic landmarks of the patient during the 3D scanning process. The recognition markers, alone or in combination with other tracking devices, such as inertial measurement units (IMU), may be attached to 3D scanner 32, camera 26, and/or the surgeon (e.g. through headset 12).

In some embodiments, 3D mapping of the surface of the body can be determined through the use of 3D scanner 32, camera 26, and/or for example, spatial transducers, for example, electromagnetic, low energy Bluetooth®, and/or inertial measurement units; optical markers, for example, reflective spheres, QR codes/patterns, and/or fiducials; and/or object recognition software algorithms to track a spatial position of a patient, for example, a patient's vertebral tissue, for example, vertebral bodies and/or a back of the patient and update a digital representation in real time.

In some embodiments, headset 12 includes sensor 28, motion sensors, acoustic/audio sensors (where the audio is transmitted to speakers (not shown) on headset 12), laser rangefinders, and/or visual sensors. In some embodiments, headset 12 includes sensor 28 and additional sensors including accelerometers, magnetometers, and/or gyroscopes which measure motion and direction in space of headset 12 and enables translational movement of headset 12 in an augmented environment.

3D mapping of the surface of the body and/or image 18 of the vertebral tissue is registered via processor 24 functioning as a registration processor. In some embodiments, processor 24 registers 3D mapping of the surface of the body and/or image 18 of the vertebral tissue and surgical treatment configuration image 23. In some embodiments, the registered images can be uploaded to a computer 42, as described herein, external to headset 12. The registered 3D mapping of the surface of the body and/or image 18 of the vertebral tissue will be automatically blended with body image 20. The registered images can be displayed on headset 12 and/or can be projected over the patient as a holographic overlay.

Lens 30 includes a screen that employs holographic display technology, for example, optical waveguides to display holograms, image guidance, and/or other digital information in real-time. In some embodiments, headset 12 via lens 30 displays a 360° view through the patient of image 18 of the vertebral tissue, body image 20 and/or surgical treatment configuration image 23. In some embodiments, headset 12 includes, for example, goggles or glasses (see, for example, similar goggles or glasses of HoloLens® or HoloLens® 2 (Microsoft Corporation, Redmond, Wash., USA); or Magic Leap® (Magic Leap, Inc, Florida, USA) and/or DreamGlass® (Dreamworld, Calif., USA)).

In some embodiments, headset 12 employs holographic display technology where light particles (e.g., photons) bounce around in a light engine within the device. The light particles enter through two lenses 30 of the headset 12 where the light particles ricochet between layers of blue, green and red glass before reaching the back of the surgeon's eyes. Holographic images form when the light is at a specific angle. In some embodiments, headset 12 includes a contact lens and/or an eye loop. In some embodiments, headset 12 includes a handheld device including, for example, a tablet or a smartphone. In some embodiments, system 10 includes projector technology including a display plate as an alternative to headset 12 or in addition to headset 12.

Figure 3:
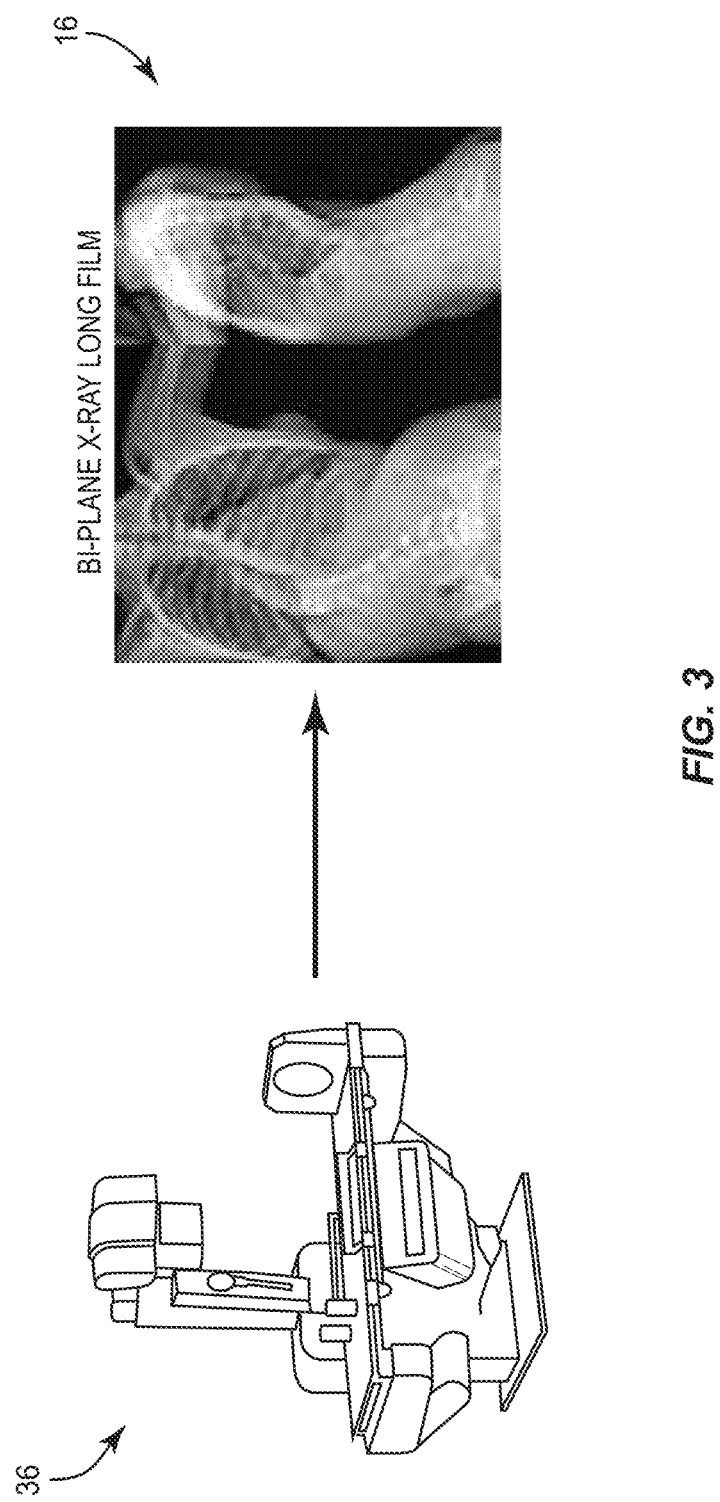
FIG. 3 is a perspective view of components of one embodiment of a diagnosis and treatment planning system including a representation of imaging of vertebrae in accordance with the principles of the present disclosure.
Figure 4:
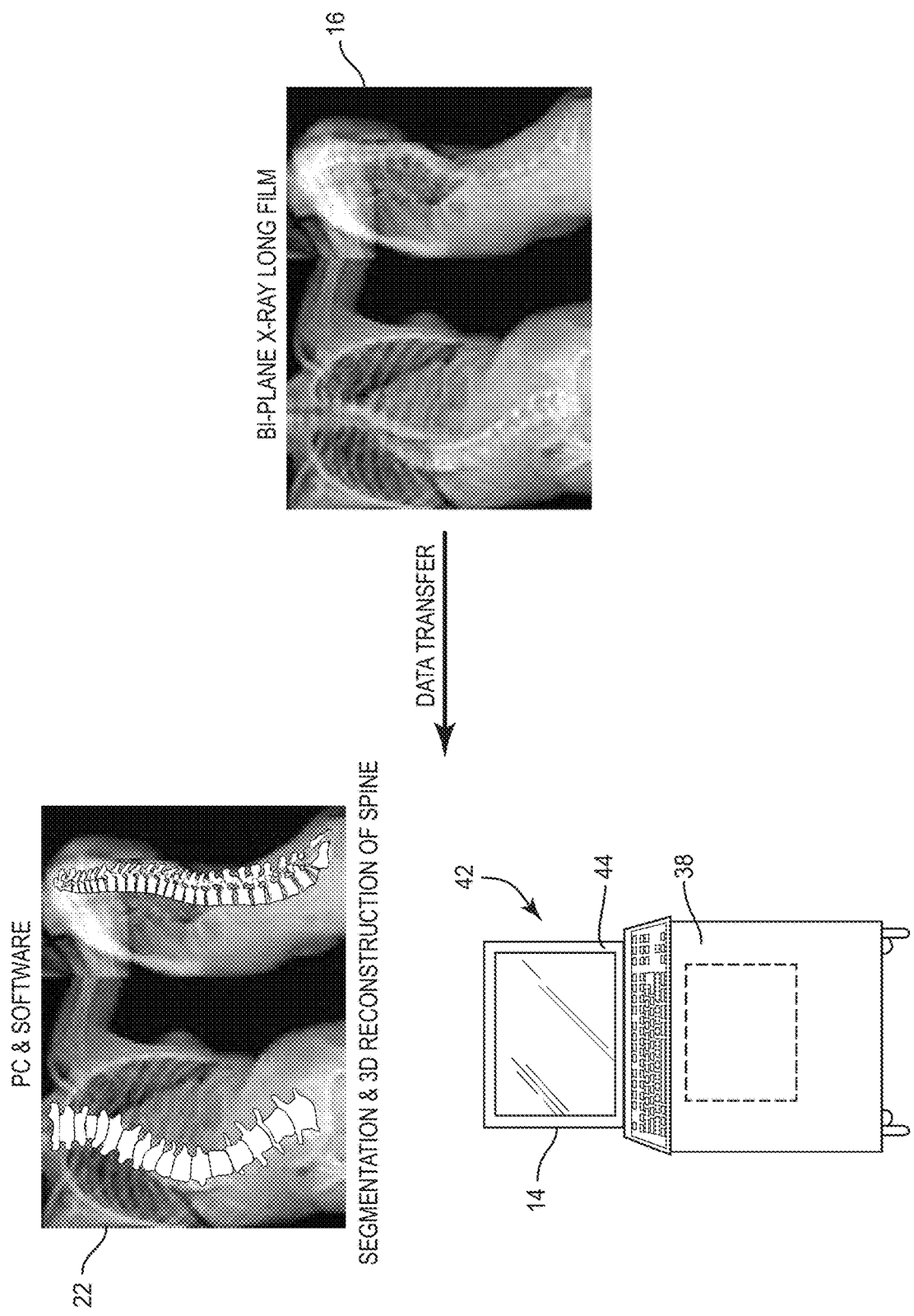
FIG. 4 is a schematic diagram illustrating components of one embodiment of a diagnosis and treatment planning system including a representation of imaging and steps of one or more embodiments of a method in accordance with the principles of the present disclosure.

Imaging 16 is generated by an imaging device 36, as shown in FIG. 3. Imaging device 36 is configured to generate images of a selected portion of the patient's anatomy, for example, vertebral tissue. Imaging device 36 is configured to generate 2D images. In some embodiments, imaging device 36 includes, for example, radiography, including, for example, an X-ray or a bi-plane X-ray long film. Imaging 16 is converted into image data to store within database 14. In some embodiments, imaging 16 is converted into image data by a software program. In some embodiments, the data points of imaging 16 can be transmitted wirelessly or uploaded into headset 12. In some embodiments, a software program is implemented for processing imaging 16 (e.g., a 2D image, for example, the bi-plane X-ray long film image) to reconstruct imaging 16 into 3D anatomy such that the practitioner has freedom to view the patient images from any angle/orientation and to see anatomy data accurately positioned on the patient. In some embodiments, the software program can include EOS software programs (see, for example, the software programs sold by EOS Imaging, Inc. having a place of business in St. Paul, Minn.).

In some embodiments, real-time mapping of the patient's back curvature to update imaging of the patient's vertebrae can occur as the patient is examined with flexation, extension and/or lateral bending maneuvers. In some embodiments, during imaging 16, patient anatomy is flexed at an appropriate location and is tracked with the patient's position as the practitioner examines the patient.

In some embodiments, imaging device 36 is configured to generate 3D images. In some embodiments, imaging device includes a CT scan, an MR scan, ultrasound, positron emission tomography (PET), and/or C-arm cone-beam computed tomography.

Database 14 is stored on a tangible storage device 38 that includes computer-readable instructions. In some embodiments, storage device 38 includes a hard drive of computer 42. In some embodiments, storage device 38 is an external hard drive unit. In some embodiments, storage device 38 includes a magnetic storage device, for example, a floppy diskette, magnetic strip, SuperDisk, tape cassette, or zip diskette; an optical storage device, for example, a Blu-ray disc, CD-ROM disc, CD-ft CD-RW disc, DVD-R, DVD+R, DVD-RW, or DVD+RW disc; and/or flash memory devices, for example, USB flash drive, jump drive, or thumb drive, CompactFlash (CF), M.2, memory card, MMC, NVMe, SDHC Card, SmartMedia Card, Sony Memory Stick, SD card, SSD or xD-Picture Card. In some embodiments, storage device 38 includes online storage, cloud storage, and/or network media storage. In some embodiments, headset 12 can access database 14/storage device 38 wirelessly.

Figure 5:
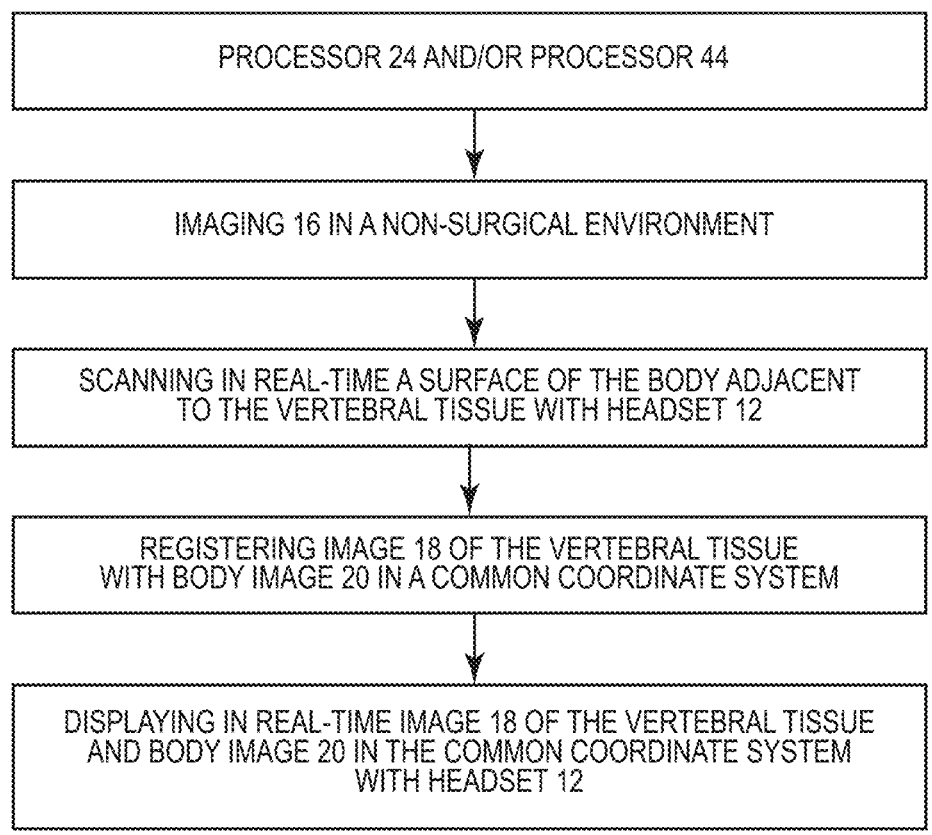
FIG. 5 is a flow diagram illustrating representative steps of one or more embodiments of a method and a diagnosis and treatment planning system in accordance with the principles of the present disclosure.

As shown in FIG. 5, processor 24 and/or a processor 44, for example, a CPU of computer 42 execute the instructions in operation of system 10. Processor 24 and/or processor 44 execute instructions for imaging 16 in a non-surgical environment, scanning in real-time a surface of the body adjacent to the vertebral tissue with headset 12; registering image 18 of the vertebral tissue with body image 20 in a common coordinate system; and displaying in real-time image 18 of the vertebral tissue and body image 20 in the common coordinate system with headset 12. In some embodiments, processor 24 and/or processor 44 further determine surgical treatment configuration 22 for the vertebral tissue.

Figure 6:
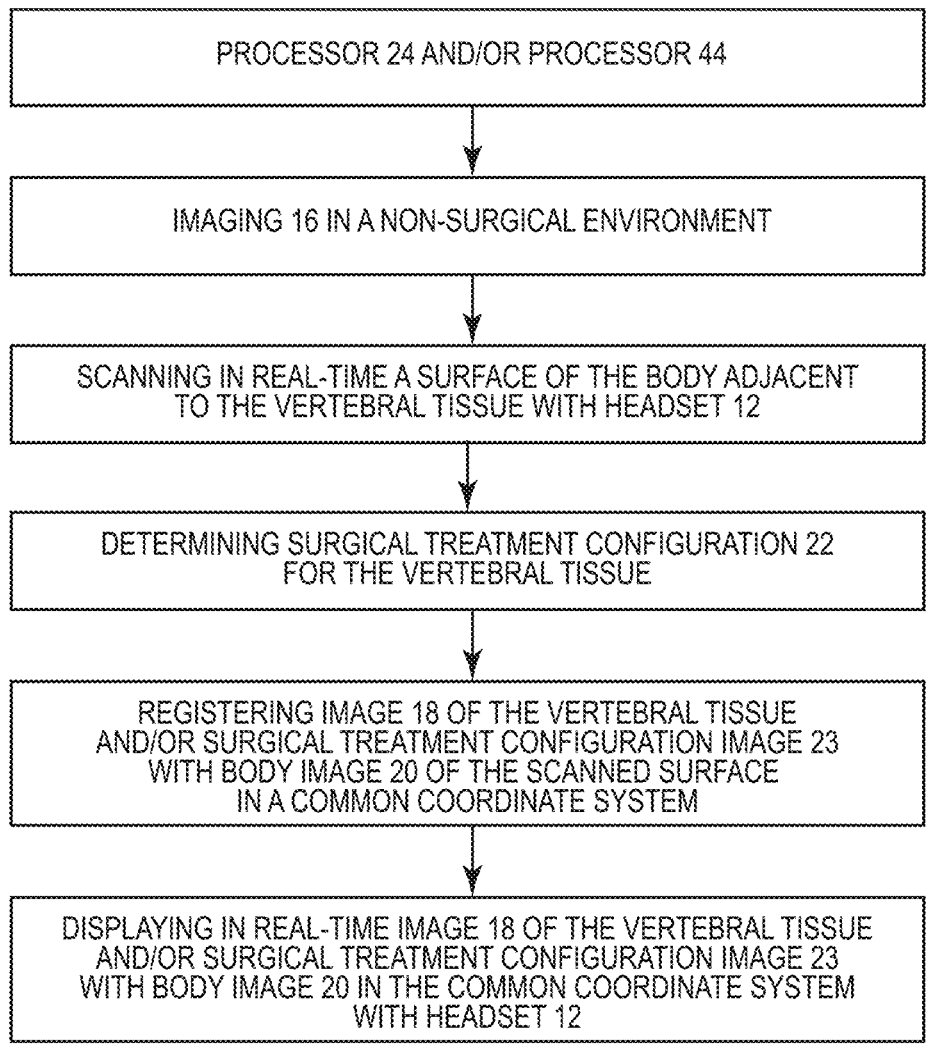
FIG. 6 is a flow diagram illustrating representative steps of one or more embodiments of a method and a diagnosis and treatment planning system in accordance with the principles of the present disclosure.

As shown in FIG. 6, processor 24 and/or processor 44 execute instructions for imaging 16 in a non-surgical environment; scanning in real-time a surface of the body adjacent to the vertebral tissue with headset 12; determining surgical treatment configuration 22 for the vertebral tissue; registering image 18 of the vertebral tissue and/or surgical treatment configuration image 23 with body image 20 of the scanned surface in a common coordinate system; and displaying in real-time image 18 of the vertebral tissue and/or surgical treatment configuration image 23 with body image 20 in the common coordinate system with headset 12.

Figure 7:
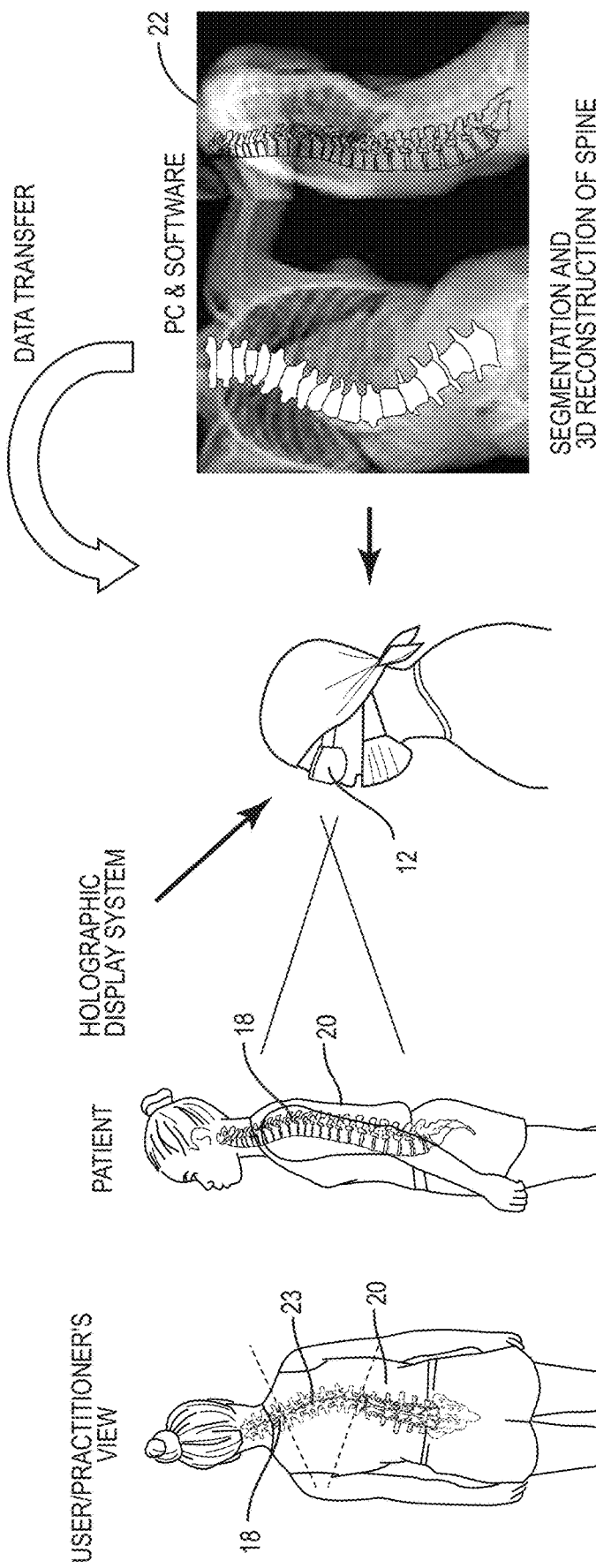
FIG. 7 is a schematic diagram illustrating components of one embodiment of a diagnosis and treatment planning system including a representation of imaging and steps of one or more embodiments of a method in accordance with the principles of the present disclosure.

Computer 42 generates surgical treatment configuration 22, as shown in FIG. 7 via a software program. In some embodiments, the software program includes, for example, Mazor X™, Mazor X™ Align, and/or Stealthstation™ sold by Medtronic Navigation, Inc. having a place of business in Louisville, Colo. In some embodiments, the software program is 3D image processing software that includes software algorithms employed for the procedure planning including for example, software algorithms for importing, thresholding, masking, segmentation, cropping, clipping, panning, zooming, rotating, measuring and/or registering. The software program is preloaded onto computer 42, the surgical treatment configuration 22 is generated by the software program, and the surgical treatment configuration 22 is uploaded onto headset 12 where graphics processor 25 renders surgical treatment configuration image 23 so that it is outputted from lens 30 for display. In some embodiments, the software program is alternatively preloaded onto headset 12, surgical treatment configuration 22 is generated from the software and headset 12 displays surgical treatment configuration image 23 from lens 30.

In some embodiments, headset 12 implements software algorithms, for example, object recognition software algorithms that are implemented for spatially locating the holograms (e.g., image 18 of the vertebral tissue and/or surgical treatment configuration image 23) and for displaying digital information relative to patient anatomy. In some embodiments, machine learning algorithms are employed that identify patient anatomical structures in patient images (e.g., imaging 16) for image segmentation and 3D model generation as well as to identify patient external anatomy for spatial placement of holographic images. In some embodiments, machine learning algorithms generate automated measurements of spinal alignment parameters in patient images, for example, including a cobb angle, pelvic tilt, pelvic incidence, sacral slope, lumbar lordosis, thoracic kyphosis, cervical lordosis, and/or sagittal vertical axis.

In some embodiments, during a physical examination and/or imaging 16 while the patient is moving, for example, flexing and/or extending, a medical practitioner has the ability to label, including, for example, annotating an area of interest and/or locations where a patient is experiencing pain directly onto imaging 16. In some embodiments, the label assists the medical practitioner during a surgical procedure.

In assembly, operation and use, diagnosis and treatment planning system 10, similar to the systems and methods described herein, is employed with a method for spinal disorder diagnosis and treatment planning. Diagnosis and treatment planning system 10 may also be employed prior to a surgical procedure, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

In one embodiment, diagnosis and treatment planning system 10, similar to the components of the systems and methods described herein, is employed in connection with one or more spinal disorder diagnosis and treatment plans. See, for example, the embodiments and disclosure of systems and methods for spinal disorder diagnosis and treatment planning, shown and described in commonly owned and assigned U.S. patent application Ser. No. 16/855,695 filed, Apr. 20, 2020, and published as U.S. Patent Application Publication No. 2021/0330250, on Oct. 28, 2021, the entire contents of which being incorporated herein by reference.

Figure 11:
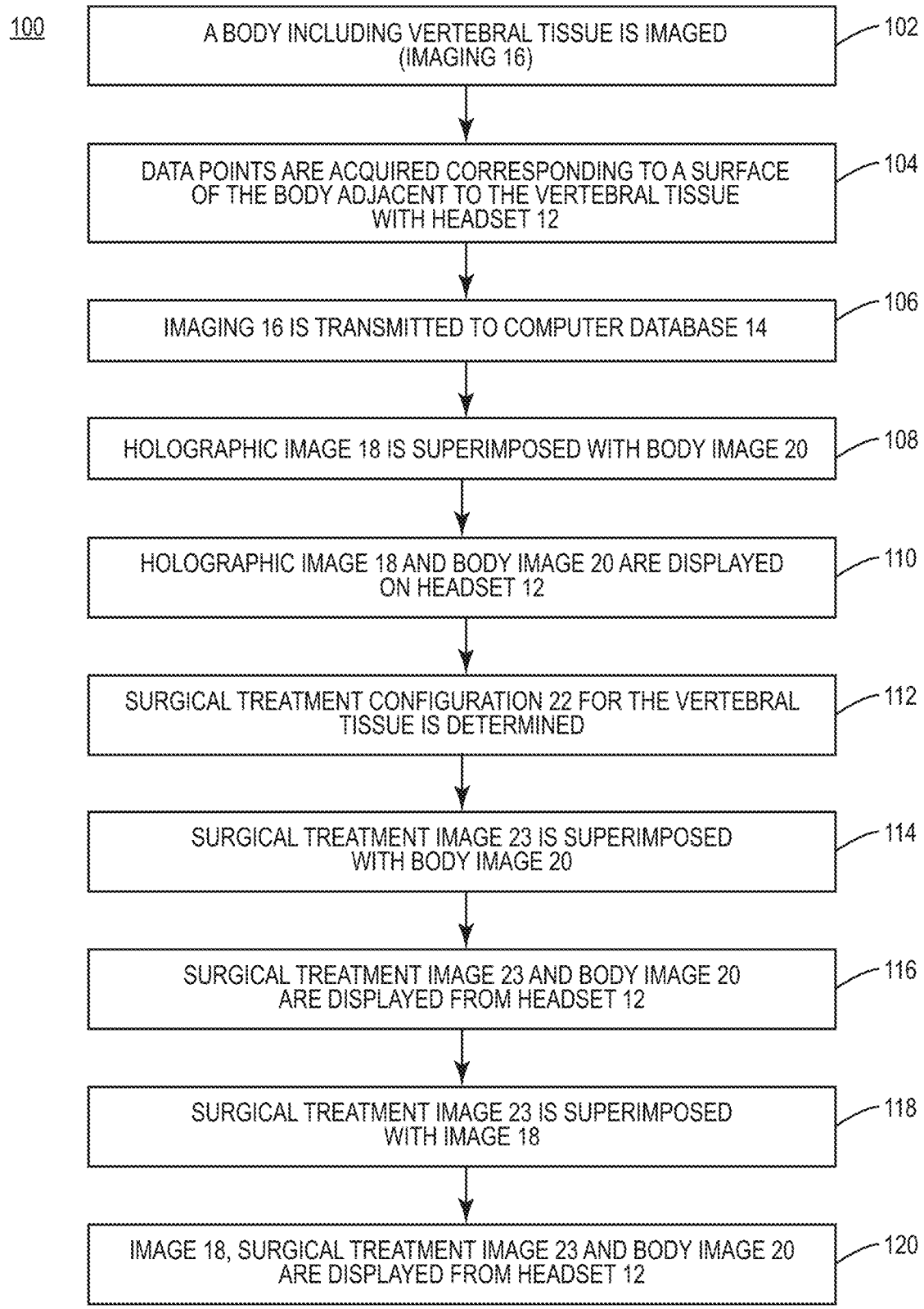
FIG. 11 is a flow diagram illustrating representative steps of one or more embodiments of a method and a diagnosis and treatment planning system in accordance with the principles of the present disclosure.

In some embodiments, system 10 includes a method 100 for spinal disorder diagnosis and treatment planning, as shown in FIG. 11. In a step 102, a body including vertebral tissue of a patient is imaged to generate imaging 16. The body is imaged via an imaging device 36. In some embodiments, imaging device 36 includes radiography, including, for example, an X-ray or a bi-plane X-ray long film. In some embodiments, imaging includes imaging the body in a non-surgical environment, as described herein.

In a step 104, data points are acquired corresponding to a surface of the body adjacent to the vertebral tissue with a mixed reality holographic display. The mixed reality display includes headset 12. Headset includes processor 24, camera 26 and sensor 28. Camera 26 is a depth sensing camera, as described herein. In some embodiments, the mixed reality display includes a handheld device. In a step 106, imaging 16 is transmitted to computer database 14. In some embodiments, imaging 16 is converted to data points by a software program, as described above. Computer database 14 is located on computer 42. In a step 108, holographic image 18 of the vertebral tissue is superimposed with body image 20 including the surface of the patient, as described herein. In a step 110, holographic image 18 of the vertebral tissue and body image 20 are displayed on headset 12. In some embodiments, holographic image 18 of the vertebral tissue superimposed with body image 20 is displayed in real-time on headset 12. In some embodiments, step 110 further includes dynamically displaying in real-time the orientation and alignment of the vertebral tissue in a non-surgical environment.

In an optional step 112, surgical treatment configuration 22 for the vertebral tissue is determined. In some embodiments, surgical treatment configuration 22 includes a segmentation of the vertebral tissue and/or a surgical reconstruction of the vertebral tissue. In some embodiments, surgical treatment configuration 22 is determined and/or generated from a software program, as disclosed above, including, for example, Mazor X™, Mazor X™ Align, and/or Stealthstation™. In an optional step 114, surgical treatment configuration holographic image 23 is superimposed with body image 20. In an optional step 116, surgical treatment configuration image 23 and body image 20 are displayed from headset 12. In an optional step 118, surgical treatment configuration image 23 is superimposed with image 18 of the vertebral tissue. In an optional step 120, image 18 of the vertebral tissue, surgical treatment configuration image 23 and body image 20 are displayed from headset 12.

Figure 12:
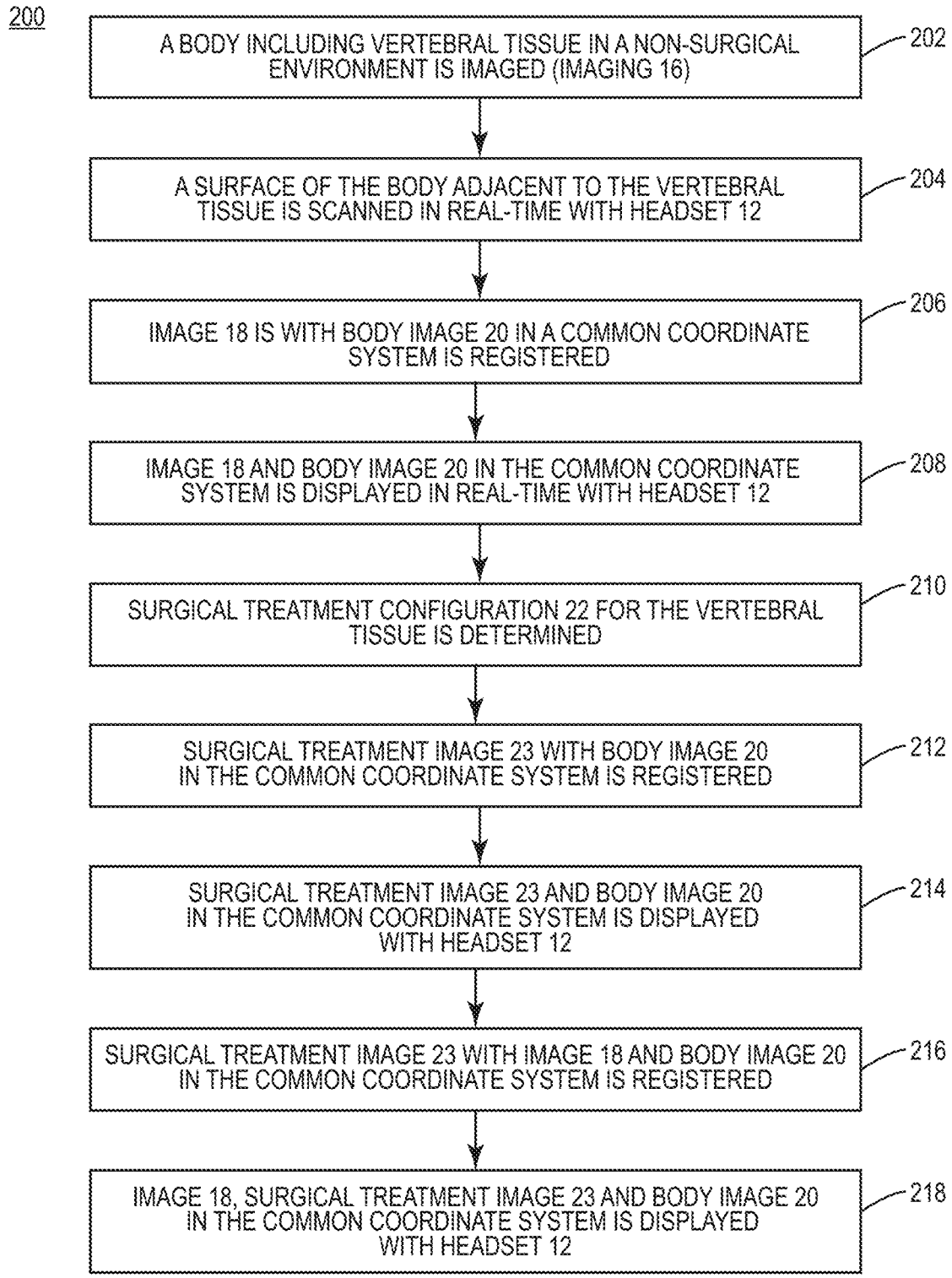
FIG. 12 is a flow diagram illustrating representative steps of one or more embodiments of a method and a diagnosis and treatment planning system in accordance with the principles of the present disclosure.

In some embodiments, system 10 includes a method 200 for spinal disorder diagnosis and treatment planning, as shown in FIG. 12, similar to method 200, as shown in FIG. 11. In a step 202, a body including vertebral tissue in a non-surgical environment is imaged to generate imaging 16. In a step 204, a surface of the body adjacent to the vertebral tissue is scanned in real-time with headset 12. Headset 12 includes camera 26 which includes, for example, a depth sensing camera, as described herein. In a step 206, holographic image 18 of the vertebral tissue with body image 20 of the scanned surface in a common coordinate system is registered. In a step 208, holographic image 18 of the vertebral tissue and body image 20 in the common coordinate system is displayed in real-time with headset 12. In an optional step 210, surgical treatment configuration 22 for the vertebral tissue is determined. In some embodiments, surgical treatment configuration 22 includes a segmentation of the vertebral tissue and/or a surgical reconstruction of the vertebral tissue.

In an optional step 212, surgical treatment configuration image 23 with body image 20 in the common coordinate system is registered. In an optional step 214, surgical treatment configuration image 23 and body image 20 in the common coordinate system are displayed with headset 12. In an optional step 216, surgical treatment configuration image 23 with image 18 of the vertebral tissue and body image 20 in the common coordinate system are registered. In an optional step 218, image 18 of the vertebral tissue, surgical treatment configuration image 23 and body image 20 in the common coordinate system are displayed with headset 12.

Figure 13:
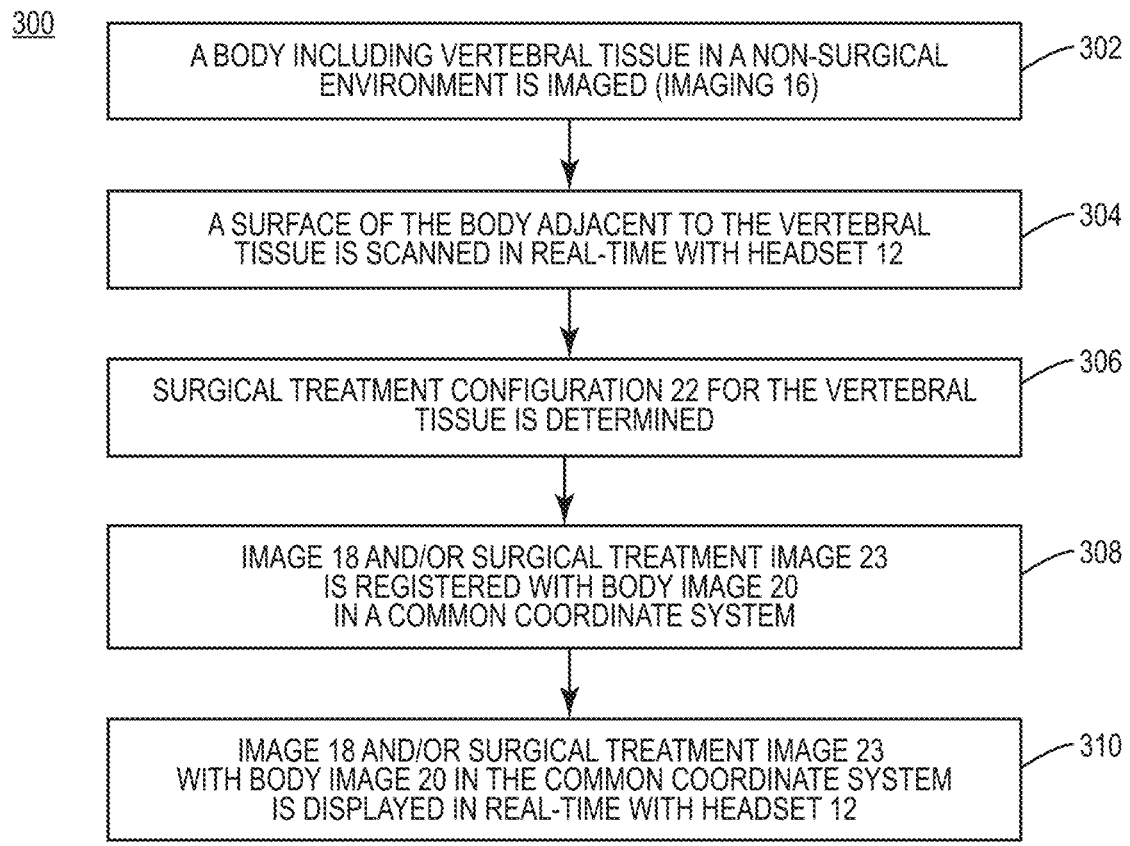
FIG. 13 is a flow diagram illustrating representative steps of one or more embodiments of a method and a diagnosis and treatment planning system in accordance with the principles of the present disclosure.

In some embodiments, system 10 includes a method 300 for spinal disorder diagnosis and treatment planning, as shown in FIG. 13, similar to method 100, as shown in FIG. 11 and method 200, as shown in FIG. 12. In a step 302, a body including vertebral tissue in a non-surgical environment is imaged to generate imaging 16. In a step 304, a surface of the body adjacent to the vertebral tissue is scanned in real-time with headset 12. In a step 306, surgical treatment configuration 22 for the vertebral tissue is determined. In a step 308, image 18 of the vertebral tissue and/or surgical treatment configuration image 23 is registered with body image 20 of the scanned surface in a common coordinate system. In a step 310, image 18 of the vertebral tissue and/or surgical treatment configuration image 23 with body image 20 in the common coordinate system is displayed in real-time with headset 12.

In some embodiments, an image guidance system, navigation system and/or a robotic guidance system, are employed with system 10, method 100, method 200 and/or method 300 if after diagnosing and treatment planning, a surgical procedure is desired. See, for example, similar surgical navigation components and their use as described in U.S. Pat. Nos. 6,021,343, 6,725,080, 6,796,988, the entire contents of each of these references being incorporated by reference herein. See, for example, STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal disorder diagnosis and treatment planning system comprising:
    a mixed reality holographic display including at least one processor, at least one camera, at least one sensor, and being configured to acquire data points corresponding to a surface of a body adjacent to vertebral tissue; and
    a computer database configured to transmit imaging of the body including the vertebral tissue to the mixed reality holographic display, the mixed reality holographic display being configured to display a first holographic image of the vertebral tissue superimposed with a body image including the surface;
    wherein the mixed reality holographic display is configured to transmit the data points to the computer database and the computer database is configured to determine a surgical treatment configuration for the vertebral tissue.

2. A system as recited in claim 1, wherein the mixed reality holographic display is configured to display the first holographic image superimposed with the body image in real-time.

3. A system as recited in claim 1, wherein the mixed reality holographic display is configured to dynamically display in real-time the orientation and alignment of the vertebral tissue in a non-surgical environment.

4. A system as recited in claim 1, wherein the surgical treatment configuration includes a segmentation of the vertebral tissue and/or a surgical reconstruction of the vertebral tissue.

5. A system as recited in claim 4, wherein the mixed reality holographic display is configured to display a second holographic image of the surgical treatment configuration superimposed with the body image.

6. A system as recited in claim 4, wherein the mixed reality holographic display is configured to display the first holographic image, the second holographic image and the body image.

7. A system as recited in claim 1, wherein the data points include three dimensional mapping of the surface.

8. A system as recited in claim 1, wherein the mixed reality holographic display has at least one sensor including a three dimensional scanner for acquiring the data points and at least one processor including a registration processor for superimposing the first holographic image with the body image.

9. A system as recited in claim 1, wherein the imaging includes a radiograph.

10. A system as recited in claim 8, wherein recognition markers are positioned relative to the surface to provide anatomic landmarks for the three dimensional scanner.

11. A system as recited in claim 1, wherein the mixed reality holographic display includes at least one depth sensing camera.

12. A system as recited in claim 1, wherein the mixed reality display includes an optical see-through headset.

13. A spinal disorder diagnosis and treatment planning system comprising:
    a tangible storage device comprising computer-readable instructions;
    a mixed reality holographic headset including a central processor and a holographic processor, and one or more cameras and sensors; and
    one or more processors, executing the instructions in operation of the system for:
    imaging a body including vertebral tissue in a non-surgical environment;
    scanning in real-time a surface of the body adjacent to the vertebral tissue with the mixed reality holographic headset;
    registering a first holographic image of the vertebral tissue with a body image of the scanned surface in a common coordinate system; and
    displaying in real-time the first holographic image and the body image in the common coordinate system with the mixed reality holographic headset,
    wherein the one or more processors further determine a surgical treatment configuration for the vertebral tissue.

14. A system as recited in claim 13, wherein the surgical treatment configuration includes a segmentation of the vertebral tissue and/or a surgical reconstruction of the vertebral tissue.

15. A system as recited in claim 13, wherein the mixed reality holographic display is configured to display a second holographic image of the surgical treatment configuration registered with the body image.

16. A system as recited in claim 13, wherein the scanning includes three dimensional mapping of the surface.

17. A system as recited in claim 13, wherein the mixed reality holographic headset includes at least one depth sensing camera.

18. A spinal disorder diagnosis and treatment planning system comprising:
    a tangible storage device comprising computer-readable instructions;
    a mixed reality holographic headset including a central processor and a holographic processor, and one or more cameras and sensors; and
    one or more processors, executing the instructions in operation of the system for:
    imaging a body including vertebral tissue in a non-surgical environment;
    scanning in real-time a surface of the body adjacent to the vertebral tissue with the mixed reality holographic headset;
    registering a first holographic image of the vertebral tissue with a body image of the scanned surface in a common coordinate system;
    displaying in real-time the first holographic image and the body image in the common coordinate system with the mixed reality holographic headset; and
    determining a surgical treatment configuration for the vertebral tissue, wherein the surgical treatment configuration includes a segmentation of the vertebral tissue and/or a surgical reconstruction of the vertebral tissue.

19. A system as recited in claim 18, wherein the mixed reality holographic display is configured to display a second holographic image of the surgical treatment configuration registered with the body image.

20. A system as recited in claim 18, wherein the scanning includes three dimensional mapping of the surface.

* * * * *